US008647852B2

(12) United States Patent
Hagen

(10) Patent No.: US 8,647,852 B2
(45) Date of Patent: *Feb. 11, 2014

(54) METHOD OF STIMULATING ETHANOL PRODUCTION AND GROWTH OF AQUATIC PLANTS

(76) Inventor: Tony A. Hagen, Sioux Falls, SD (US)

(*) Notice: Subject to any disclaimer, the term of this patent is extended or adjusted under 35 U.S.C. 154(b) by 454 days.

This patent is subject to a terminal disclaimer.

(21) Appl. No.: 12/628,601

(22) Filed: Dec. 1, 2009

(65) Prior Publication Data

US 2010/0285551 A1 Nov. 11, 2010

Related U.S. Application Data

(63) Continuation of application No. 12/437,333, filed on May 7, 2009.

(51) Int. Cl.
*C12P 7/10* (2006.01)
*C12P 7/08* (2006.01)
*A61K 36/00* (2006.01)

(52) U.S. Cl.
USPC ............................. 435/165; 435/163; 424/725

(58) Field of Classification Search
None
See application file for complete search history.

(56) References Cited

U.S. PATENT DOCUMENTS

| | | | |
|---|---|---|---|
| 4,062,146 | A | 12/1977 | Grossman et al. |
| 4,324,068 | A | 4/1982 | Anthony |
| 4,532,210 | A | 7/1985 | Miura et al. |
| 4,557,310 | A | 12/1985 | Castellaw et al. |
| 6,395,521 | B1 | 5/2002 | Miura |
| 7,135,308 | B1 | 11/2006 | Bush et al. |
| 8,143,041 | B2 | 3/2012 | Hagen |
| 2003/0024874 | A1 | 2/2003 | Wallace et al. |
| 2005/0061737 | A1 | 3/2005 | Linden et al. |
| 2007/0062105 | A1 | 3/2007 | Stevens |
| 2008/0153080 | A1 | 6/2008 | Woods et al. |
| 2008/0176304 | A1 | 7/2008 | Lee |
| 2010/0285554 | A1* | 11/2010 | Hagen ............................ 435/165 |
| 2011/0045561 | A1 | 2/2011 | Hagen |
| 2011/0086400 | A1 | 4/2011 | Hagen |
| 2011/0086401 | A1 | 4/2011 | Hagen |
| 2011/0086419 | A1 | 4/2011 | Hagen |
| 2013/0071902 | A1 | 3/2013 | Hagen et al. |

FOREIGN PATENT DOCUMENTS

| | | |
|---|---|---|
| EP | 0645456 A1 | 3/1995 |
| WO | WO2007101172 A2 | 9/2007 |
| WO | WO2008039450 A2 | 4/2008 |
| WO | WO2008047113 A2 | 4/2008 |

OTHER PUBLICATIONS

Ueno, Y., Kurano, N., Miyachi, S. (1998) Ethanol Production by Dark Fermentation in the Marine Green Alga, *Chlorococcum littorale* J. Ferment. Bioengineer. vol. 86, No. 1 pp. 38-43.*

Li, Y., Xie, Y., Ren, B., Luo, W., Huang, J. (2007) Oxygen enhances the recovery of *Potamogeton maackianus* from prolonged exposure to very low irradiance. Aquatic Botany 86 pp. 295-299.*
Summers, J.E., Ratcliffe, R.G., Jackson, M. (2000) Anoxia tolerance in the aquatic monocot *Potamogeton pectinatus*: absence of oxygen stimulates elongation in association with an unusually large Pasteur effect. J. Exper. Botany, vol. 51, No. 349, pp. 1413-1422.*
Journal of Experimental Botany vol. 51, No. 349 pp. 1413-1422 Aug. 2000.
Aquatic Botany 86 (2007) 295-299.
European Search Report issued in EP Application No. 10772632, completed Oct. 11, 2012, 8 pages.
Luo, Dexin et al., "Life Cycle Energy and Greenhouse Gas Emissions for an Ethanol Production Process Based on Blue-Green Algae", Environmental Science & Technology, vol. 44, No. 22, Nov. 2010, pp. 8670-8677, XP002684824, ISSN: 0013-936X.
Saygideger, Saadet Demirors et al., "Effect of 2,4-dichlorophenoxyacetic acid on growth, protein and cholorphyll-a content of *Chlorella vulgaris* and *Spirulina platensis* cells", Journal of Environmental Biology, vol. 29, No. 2, Mar. 2008, pp. 175-178.
Summers, Jacky E. et al., "Anoxia tolerance in the aquatic monocot *Potamogeton pectinatus*: Absence of oxygen stimulates elongation in association with an unusually large Pasteur effect", Journal of Experimental Botany, vol. 51, No. 349, Aug. 2000, pp. 1413-1422.
Ailstock, M. Stephen "The Characterization of Axenic Culture Systems Suitable for Plant Propagation and Experimental Studies of the Submersed Aquatic Angiosperm *Potamogeton pectinatus*" vol. 14, No. 1, p. 57-64 Mar. 1991.
Anderson, Lars W.J., "A review of aquatic weed biology and management research conducted by the United States Department of Agriculture—Agricultural Research Service" Pest Manag Sci 59:801-813 (online: 2003) DOI: 10.1002/ps.725.
Baldantoni, Daniela, "Analyses of three native aquatic plant species to assess spatial gradients of lake trace element contamination" Aquatic Botany 83 (2005) 48-60.
Colmer, T.D., "Root aeration in rice (*Oryza saliva*): evaluation of oxygen, carbon dioxide, and ethylene as possible regulators of root acclimatizations" New Phytologist (2006) 170: 767-778.
Colmer, Timothy, "Blackwell Publishing Ltd Underwater photosynthesis and respiration in leaves of submerged wetland plants: gas films improve CO2 and O2 exchange" New Phytologist (2008) 177: 918-926.
Crump, Byron, "Attached Bacterial Populations Shared by Four Species of Aquatic Angiosperms" Applied and Environmental Microbiology,Oct. 2008, p. 5948-5957 vol. 74, No. 19.
Dixon, M.H., "Physiological and Metabolic Adaptations of *Potamogeton pectinatus* L. Tubers Support Rapid Elongation of Stem Tissue in the Absence of Oxygen" Plant Cell Physiol. 47(1): 128-140 (2006).

(Continued)

*Primary Examiner* — Chris R Tate
*Assistant Examiner* — Russell Fiebig
(74) *Attorney, Agent, or Firm* — Faegre Baker Daniels LLP

(57) ABSTRACT

A method of stimulating ethanol production and growth of aquatic plants includes the steps of placing aquatic plants in a cell containing water and creating an oxygenated condition within the cell to initiate an aerobic process. The aquatic plants create and store carbohydrates during the aerobic process. The cell is then covered with a light blocking cover during the anoxic condition to inhibit light from entering the cell. An anoxic condition is created within the cell to initiate an anaerobic process by the aquatic plants. The aquatic plants increase in size and release ethanol into the water by metabolism of stored carbohydrates during the anaerobic process. The ethanol is then sequestered from the water.

24 Claims, 2 Drawing Sheets

(56) References Cited

OTHER PUBLICATIONS

Ghobrial, M.G., "Influence of Barley Straw and Submerged Macrophytes on Fishpond Wastewater Quality" vol. 33 No. 3, 2007: 68-87.

Greger, Maria, et al., "A Tentative Model of Cd Uptake in *Potamogeton pectinatus* in Relation to Salinity" vol. 35, No. 2, pp. 215 225, 1995.

Gruber, Renee., et al.,"Feedback effects in a coastal canopy-forming submersed plant bed" Limnol. Oceanogr., 55(6), 2010, 2285-2298.

Hangelbroek, Helen H. et al., "Local adaptation of the pondweed *Potamogeton pectinatus* to contrasting substrate types mediated by changes in propagule provisioning" Journal of Ecology 2003 91, 1081-1092.

Harada, Taro, et al., "Anoxia-enhanced expression of genes isolated by suppression subtractive hybridization from pondweed (*Potamogeton distinctus* A. Benn.) turions" Planta (2007) 226:1041-1052.

Harada, Taro, et al., "Starch Degradation and Sucrose Metabolism During Anaerobic Growth of Pondweed (*Potamogeton distinctus* A. Benn.) Turions" Plant and Soil 253: 125-135, 2003.

Harada, Taro, et al.. "Expression of Sucrose Synthase Genes Involved in Enhanced Elongation of Pondweed (*Potamogeton distinctus*) Turions under Anoxia" Annals of Botany 96: 683-692, 2005.

Hidding, Bert, et al., "How a Bottom-Dweller Beats the Canopy: Inhibition of an Aquatic Weed (*Potamogeton pectinatus*) by Macroalgae (*Chara* spp.)", Freshwater Biology (2010) 55, 1758-1768.

Huang, Shaobai, et. al., "Manipulation of Ethanol Production in Anoxic Rice Coleoptiles by Exogenous Glucose Determines Rates of Ion Fluxes and Provides Estimates of Energy Requirements for Cell Maintenance During Anoxia, " Journal of Experimental Botany, vol. 56, No. 419, pp. 2453-2463, Sep. 2005.

International Search Report issued in PCT/US2010/033335, mailed Dec. 17, 2010.

International Search Report issued in PCT/US2010/058174, mailed mailed Aug. 30, 2011, 14 pages.

Ishizawa, K., "Growth and Energy Status of Arrowhead Tubers, Pondweed Turions and Rice Seedlings Under Anoxic Conditions," Plant, Cell and Environment (1999) 22, (505-514).

Jackson, Michael B., "Evolution and Mechanisms of Plant Tolerance to Flooding Stress," Annals of Botany 103: 137-142, 2009.

James, William F., "Effects of Lime-Induced Inorganic Carbon Reduction on the Growth of Three Aquatic Macrophyte Species," Aquatic Botany 88 (2008) 99-104.

Janssen, Marcel et al., "Scale-up aspects of photobioreactors: effects of mixing-induced light/dark cycles", Journal of Applied Phycology, 2000, vol. 12, pp. 225-237.

Kennedy, Thomas L., "The Effects of Nitrate Loading on the Invasive Macrophyte *Hydrilla verticillata* and Two Common, Native Macrophytes in Florida," Aquatic Botany 91 (2009) 253-256.

Koizumi, Yayoi, "Involvement of Plasma Membrane H+-Atpase in Anoxic Elongation of Stems in Pondweed (*Potamogeton distinctus*) Turions," New Phytologist © 2011 New Phytologist Trust, doi: 10.1111/j.1469-8137.2010.03605.x, 10 pages.

Miller, Stephanie, A., "Mechanisms of Resistance of Freshwater Macrophytes to Herbivory by Invasive Juvenile Common Carp," Freshwater Biology (2007) 52, 39-49.

Mishima, D. et al., "Ethanol production from candidate energy crops: Water hyacinth (*Eichnornia crassipes*) and water lettuce (*Pistia stratiotes* L.) Bioresource Technology 99:2495-2500 2008.

Miura, Y. et al., "Stimulation of hydrogen production in Algal Cells Grown Under High C(2 Concentration and Low Temperature", Applied Biochemistry and Biotechnology, copyright 1993, vol. 39/40, pp. 753-761.

Ookawara, Ryuto, "Expression of a-Expansin and Xyloglucan Endotransglucosylase/Hydrolase Genes Associated with Shoot Elongation Enhanced by Anoxia, Ethylene and Carbon Dioxide in Arrowhead (*Sagittaria pygmaea* Miq.) Tubers," Annals of Botany 96: 693-702, 2005.

Rozentsvet, O.A., "Lipid Composition of *Potamogeton pectinatus* As a Function of Water Contamination," Chemistry of Natural Compounds, vol. 46, No. 5, 2010.

Sato, Tatsuhisa, "Stimulation of Glycolysis in Anaerobic Elongation of Pondweed (*Potamogeton distinctus*) Turions," Journal of Experimental Botany, vol. 53, No. 376, pp. 1847-1856, Sep. 2002.

Smart, R. Michael, "Techniques for Establishing Native Aquatic Plants," J. Aquat. Plant Manage. 36: 44-49 (1998).

Spencer, David F. et al., "Soluble Sugar Concentrations Associated with Tuber and Winter Bud Sprouting", J. Aquat. Plant Manage. 39:45-47 (2001).

Spencer, David F., "Competition between two submersed aquatic macrophytes, *Potamogeton pectinatus* and *Potamogeton gramineus*, across a light gradient," Aquatic Botany 92 (2010) 239-244.

Spencer, David F., "Construction costs for some aquatic plants," Aquatic Botany 56 (1997) 203- 214.

Spencer, David F., "Dilute Acetic Acid Exposure Enhances Electrolyte Leakage by *Hydrilla verticillata* and *Potamogeton pectinatus* Tubers," J. Aquat. Plant Manage. 35: 25-30 (1997).

Spencer, David F., "Emergence of vegetative propagules of *Potamogeton nodosus*, *Potamogeton pectinatus*, *Vallisneria americana*, and *Hydrilla verticillata* based on accumulated degree-days," Aquatic Botany 67 (2000) 237-249.

Spencer, David F., "Influence of Propagule Size, Soil Fertility, and Photoperiod on Growth and Propagule Production by Three Species of Submersed Macrophytes," Wetlands, vol. 15, No. 2, Jun. 1995, pp. 134-140.

Summers, Jacky E., "Anaerobic promotion of stem extension in *Potamogeton pectinatus*. Roles for carbon dioxide, acidification and hormones," Physrologia Plantarum 96: 615-622. 1996.

Summers, Jacky E., "Light- and Dark-Grown *Potamogeton pectinatus*, An Aquatic Macrophyte, Make No Ethylene (Ethene) But Retain Responsiveness to the Gas," Aust. J. Plant Physiol., 1998, 25, 599-608.

Sutton, David L., "Influence of Allelochemicals and Aqueous Plant Extracts on Growth of Duckweed," J. Aquat. Plant Manage. 27: 90-95 (1989).

Tamura, Shinsuke, "Involvement of Calcium Ion in the Stimulated Shoot Elongation head Tubers under Anaerobic Conditions," Plant Cell Physiol. 42(7): 717-722 (2001).

Tauskela, Joseph S., "A Regulated Environmental Perfusion System for the Study of Anoxic or Hypoxic Cultured Neurons Using Microfluorescence Imaging and Electrophysiology," pnugers Arch—Eur J Physiol (1998) 435: 775-780.

Ueno, Yoshiyuki et al., "Ethanol Production by Dark Fermentation in the Marine Green Alga, *Chlorococcum littorale*", Journal of Fermentation and Bioengineering, vol. 86, No. 1, 38-43, 1998.

Van Den Berg, Marcel S., "Competition between *Chara aspera* and *Potamogeton pectinatus* as a function of temperature and light," Aquatic Botany 60 (1998) 241-250.

Voesenek, L.A.C.J., "The Role of Ethylene and Darkness in Accelerated Shoot Elongation of Ammophila Breviligulata Upon Sand Burial," Oecologia (1998) 115:359-365.

Winkel, Anders., "Use of Sediment CO2 by Submersed Rooted Plants," Annals of Botany 103: 1015-1023, 2009.

Woolf, Thomas E., "Seasonal Biomass and Carbohydrate Allocation Patterns in Southern Minnesota Curlyleaf Pondweed Populations," J. Aquat. Plant Manage. 41: 113-118 (2003).

Written Opinion issued in PCT/US2010/033335, mailed Dec. 17, 2010, 4 pages.

International Search Report and Written Opinion issued in PCT/2012/056261, dated Mar. 28, 2013, 11 pages.

\* cited by examiner

METHOD OF STIMULATING ETHANOL PRODUCTION AND GROWTH OF AQUATIC PLANTS

This application is a continuation in part of U.S. patent application Ser. No. 12/437,333 filed on May 7, 2009.

BACKGROUND OF THE DISCLOSURE

Field of the Disclosure

The disclosure relates to ethanol production methods and more particularly pertains to a new ethanol production method for promoting plant growth by plants which produce free ethanol during anaerobic metabolism to form a self-sustaining cycle of plant growth and ethanol production.

SUMMARY OF THE DISCLOSURE

An embodiment of the disclosure meets the needs presented above by generally comprising the steps of placing aquatic plants in a cell containing water and creating an anoxic condition within the cell to initiate an anaerobic process by the aquatic plants. The aquatic plants increase in size and release ethanol by metabolism of stored carbohydrates during the anaerobic process. An oxygenated condition is then created within the cell to initiate an aerobic process. The aquatic plants create and store carbohydrates during the aerobic process. The steps of creating anoxic and oxygenated conditions are repeated to stimulate aquatic plant growth and the release of ethanol.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawing wherein.

DESCRIPTION OF THE PREFERRED EMBODIMENT

Figure 1:
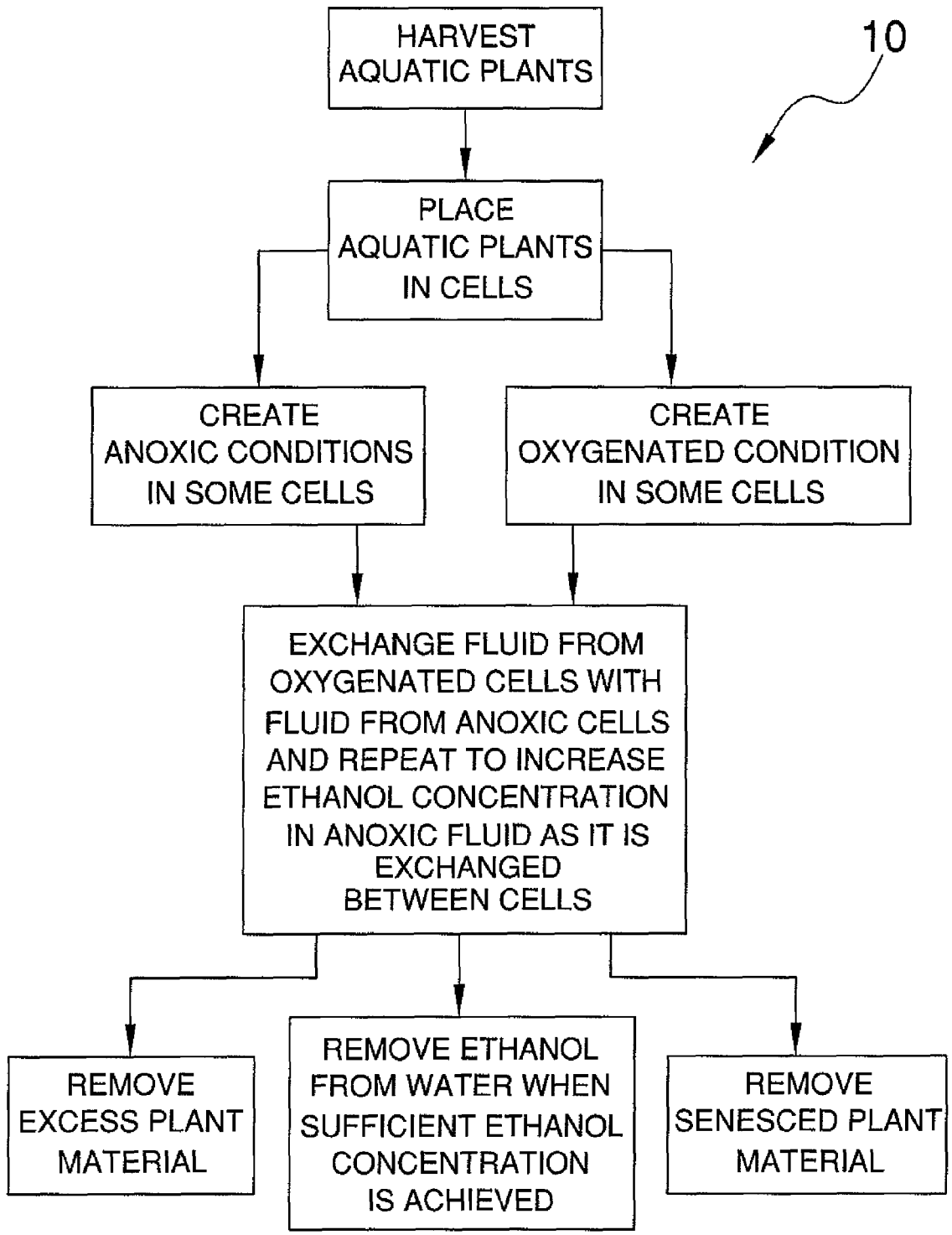
FIG. 1 is a schematic view of a method of stimulating ethanol production and growth of aquatic plants according to an embodiment of the disclosure.
Figure 2:
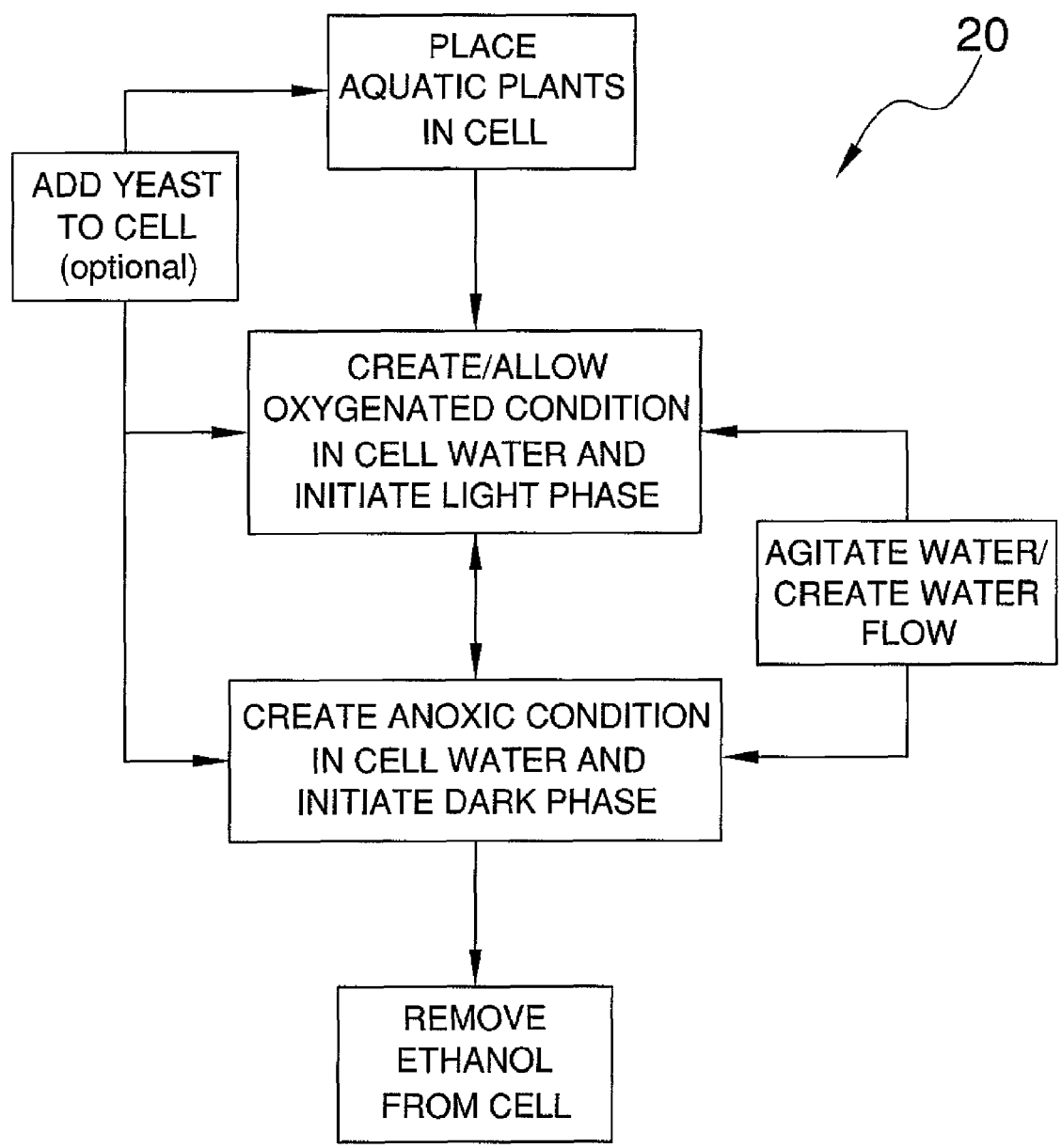
FIG. 2 is a schematic view of a method of stimulating ethanol production and growth of aquatic plants according to an embodiment of the disclosure.

With reference now to the drawings, and in particular to FIGS. 1 and 2, a new ethanol production method embodying the principles and concepts of an embodiment of the disclosure and generally designated by the reference numeral 10 will be described.

As illustrated in FIG. 1, the methods 10 and 20 of stimulating ethanol production and growth of aquatic plants generally comprises harvesting aquatic plants from lakes or ponds which are then introduced into one or more cells. As the method 10 is performed, it may be used to grow and provide aquatic plants as they are needed for future cells or for replacement purposes. The cells are constructed to hold water and may or may not be lined to prevent transfer of fluids and gases into a ground surface supporting the cell. A substrate, such as a fine particulate, is placed in the cells and the aquatic plants introduced into the cells where they can anchor themselves in the particulate. A fine particulate may used as it may promote less energy expenditure on the part of the aquatic plants to root growth into the particulate and retains a higher percentage of the plant matter above the surface of the particulate. However, many of the plants being utilized by the method 10, 20 primarily rely on their root systems as anchoring means and therefore any type of anchoring mechanism or substrate may be used which can be engaged by the roots. This may include mechanical anchoring devices, such as grids or screens, to which the roots may engage and couple themselves.

The number of cells and their size is not crucial to the method and each number and size may be dictated by available land area, access to raw materials and cost controls, though it should be understood that the method may be practiced with a single cell. The cells may have any depth required for the chosen aquatic plant to properly grow. However, it has been found that cell may have a depth of between 10 cm and 7 m to prevent restricted plant growth. The cells may also be temperature controlled and in particular the cell should be prevented from freezing which may kill the aquatic plants. Heat for the cells may be sequestered from waste heat emitted by adjacent ethanol processing plants or any other convenient source of waste heat. Depending on the variety of aquatic plant being utilized, a temperature range may be selected which optimizes plant growth and ethanol production. For example, some selected plants such as *Stuckenia pectinate* may be mainted between 85° Fahrenheit and 73° Fahrenheit.

The aquatic plants may be selected from any number of aquatic plants which readily live in or on an aquatic environment such as directly in water or in permanently saturated soil. More generally, the term "aquatic plant" may include any algae, aquatic plant or semi-aquatic plant which has a high tolerance for either being constantly submerged in water or intermittently submerged during periods of flooding. Further, more than one type of aquatic plant may be used within a single cell.

The aquatic plants may include, for example, algae, submersed aquatic herbs such as, but not limited to, *Stuckenia pectinate* (formerly known as *Potamogeton pectinatus*), *Potamogeton crispus, Potamogeton distintcus, Potamoteton nodosus, Ruppia maitima, Myriophyllum spicatum, Hydrilla verticillata, Elodea densa, Hippuris vulgaris, Aponogeton boivinianus, Aponogeton rigidifolius, Aponogeton longiplumulosus, Didiplis diandra, Vesicularia dubyana, Hygrophilia augustifolia, Micranthemum umbrosum, Eichhornia azurea, Saururus cernuus, Cryptocoryne lingua, Hydrotriche hottoniiflora, Eustralis stellata, Vallisneria rubra, Hygrophila salicifolia, Cyperus helferi, Cryptocoryne petchii, Vallisneria americana, Vallisneria torta, Hydrotriche hottoniiflora, Crassula helmsii, Limnophila sessiliflora, Potamogeton perfoliatus, Rotala wallichii, Cryptocoryne becketii, Blyxa aubertii* and *Hygrophila difformmis*, duckweeds such as, but not limited to, *Spirodela polyrrhiza, Wolffia globosa, Lemna trisulca, Lemna gibba, Lemna minor*, and *Landoltia punctata*, water cabbage, such as but not limited to *Pistia stratiotes*, buttercups such as but not limited to *Ranunculus*, water caltrop such as but not limited to *Trapa natans* and *Trapa*

*bicornis*, water lily such as *Nymphaea lotus, Nymphaeaceae* and *Nelumbonaceae*, water hyacinth such as but not limited to *Eichhornia crassipes, Bolbitis heudelotii*, and *Cabomba*, and seagrasses such as but not limited to *Heteranthera zosterifolia*, Posidoniaceae, Zosteraceae, Hydrocharitaceae, and Cymodoceaceae. Moreover, in one of the various embodiments, a host alga is selected from the group consisting of green algae, red algae, brown algae, diatoms, marine algae, freshwater algae, unicellular algae, multicellular algae, seaweeds, cold-tolerant algal strains, heat-tolerant algal strains, ethanol-tolerant algal strains, and combinations thereof.

The aquatic plants in general may also be selected from one of the plant families which include Potamogetonaceae, Ceratophyllaceae, Haloragaceae, and Ruppiaceae. More particularly, the aquatic plants chosen should have a large Pasteur effect which increases the ratio of anaerobic $CO_2$ production to the aerobic $CO_2$ production. Typically this ratio is on the order of 1:3, but aquatic plants such as for example *Stuckenia pectinata*, formerly and also sometimes known as *Potamogeton pectinatus*, and commonly known as Sago Pondweed, may increase this ratio to 2:1 as explained in "Anoxia tolerance in the aquatic monocot *Potamogeton pectinatus*: absence of oxygen stimulates elongation in association with an usually large Pasteur effect," Journal of Experimental Botany, Volume 51, Number 349, pp. 1413-1422, August 2000, which is incorporated herein by reference. During an elongation process which takes place in an anoxic environment, the plant elongates to form cellular chambers which will later be used to store carbohydrates formed during aerobic metabolism through an aerobic process of the aquatic plant. These carbohydrates can then be used to release ethanol during anaerobic metabolism through an anaerobic process of the aquatic plant. Generally, the equations are as follows:

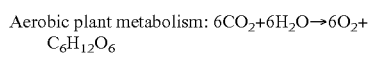

Aerobic plant metabolism: $6CO_2 + 6H_2O \rightarrow 6O_2 + C_6H_{12}O_6$

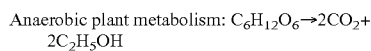

Anaerobic plant metabolism: $C_6H_{12}O_6 \rightarrow 2CO_2 + 2C_2H_5OH$

Once the aquatic plants are in a cell, the water in the cell is placed in an anoxic condition by introducing, originally or at a later time, anoxic water into the cell or by removing the oxygen from the water using organic or mechanical means. Alternatively, corn and/or bacteria may be added to the water to deplete the oxygen in the water. The lack of oxygen in the water initiates the anaerobic process in the aquatic plants causing them to elongate and to produce ethanol. This may be encouraged by the introduction of chemical catalysts and $CO_2$. One chemical catalyst which may be included is 2,4-dichlorophenoxyacetic acid. Additional nutrients and salts such as salts of potassium, nitrogen and phosphorus may further be added to promote growth of the aquatic plants. Further, depending upon the species of aquatic plant being utilized, organic substrates, including but not limited to those such as sucrose, glucose and acetate, may also be added to the cell.

During the anaerobic process, the aquatic plants will increase in size dramatically and may achieve a lengthening of up to 10 times or more of its original length. The term 'size' here is to be understood to include a volume increase of plant matter which allows for it to store a larger amount of carbohydrates. This elongation provides cellular chambers for holding carbohydrates to be later formed by the aquatic plants. Additionally during the anaerobic process, ethanol is excreted extracellularly by the aquatic plants. This ethanol is then held within the water of the cell until it is removed by conventional methods. As explained further below, the cell, when first used, may be allowed to achieve a minimum ethanol concentration which will be determined depending on the particular method being practiced. This minimum concentration will be increased through progression of the method. This step may take place from one to several days though in the case of *Potamogeton pectinatus* (or *Stuckenia pectinata*) a total of six days may suffice. The time required will depend on many factors such as light diffusion and availability of nutrients.

The next step is to stop the anaerobic process by creating an oxygenated condition within the cell which will initiate the aerobic process. This may be accomplished by introducing oxygenated water into the cell and by removing the anoxic water or allowing the water oxygenate naturally by plant releasing of oxygen. During the aerobic process, as indicated above, the aquatic plants create carbohydrates through metabolic processes and then retain the carbohydrates within their elongated structures. Waste materials, such as waste biomass from the method 10, industrial waste, municipal waste and the like may be added to the cell to provide nutrients to the aquatic plants. Additionally, maximum sunlight filtration is encouraged as is temperature regulation to promote growth of the aquatic plants. Further, the pH of the cell must be monitored to prevent acidosis of the cell. This may be counteracted with calcium buffering compounds such as calcium carbonate and calcium chlorate, but will ultimately be dependent upon the tolerances of the particular aquatic plant species in the cell. The duration of the aerobic process is likewise dependent upon a number of factors but will typically end when carbohydrate production begins to slow or reaches a predetermined level. With *Potamogeton pectinatus* (*Stuckenia pectinata*) this may be between 2 days and 14 days depending upon environmental conditions within the cell.

The use of anoxic and oxygenated water may also be combined by use of thermal strata within the cell. In particular, the coldest strata, which will be on the bottom of the cell, may remain anoxic to encourage growth while the upper strata of warmer water may include oxygenated water to encourage carbohydrate production.

Once maximum carbohydrate formation, or a predetermined level of such, is approached the oxygenated water is made anoxic to again begin the process of elongation and ethanol formation. The steps of creating anoxic conditions and oxygenated conditions are then repeated to continually promote elongation and ethanol production followed by carbohydrate production. This creates a self-sustaining cycle as the plant growth replenishes both plant matter lost to plant senescence and those plants which no longer meet established tolerances of ethanol production. Additional plant growth which cannot be used for replenishing purposes or for furnishing plant material for another cell may be removed and fermented using conventional methods to also produce ethanol. Carbon dioxide released during the fermentation process may be captured and returned to the cell to promote carbohydrate production. Plant waste, both before or after the fermentation process, may further be used for replenishing nutrients to the cell and/or may be processed for biochemical industrial usage such as in ethanol and diesel biofuels, pharmaceuticals, cosmetics, colorants, paints and the like.

As stated above, the anoxic water may be retained and used again, at least until its ethanol content approaches a lethal concentration to the aquatic plant. This concentration is dependent upon the aquatic plant being used as well the number of cells being utilized which can affect the number of times the anaerobic process can occur. Typically the method will be practiced with multiple cells wherein the anoxic water and the oxygenated water are rotated between the cells as needed to alternate between the anoxic condition and the oxygenated condition. For example, the process of utilizing multiple cells may include a first cell having anoxic water containing 2% ethanol which is moved into a second cell having previously been oxygenated. The anoxic water replaces the removed oxygenated water in the second cell to create an anoxic condition in the second cell. Within the second cell plant growth and ethanol production are then stimulated. It is noted that having ethanol originally in the second cell (since the anoxic water contains ethanol from the anaerobic process of the first cell) may further spur ethanol production when the aquatic plants detect ethanol in the water. The ethanol concentration may be allowed to increase, for example, up to 4% in the second cell. Each time the anoxic water is moved into a new cell, the elongation and ethanol production of those plants is stimulated. Once the ethanol concentration of the anoxic water reaches a predetermined level, such as for example 10% by volume, the anoxic water is removed from the cell it is now positioned in and the ethanol extracted from the water using conventional means.

The use of multiple cells allows the cycle to be used within a closed loop which again is self sustaining and will sequester carbon dioxide during the formation of carbohydrates. The method 10 grows new aquatic plants faster than they are depleted by senescing to allow for new cells to be seeded by the newly grown aquatic plants. More importantly, all plant waste may be utilized through fermentation into ethanol and processed for biochemical industries or returned to the cells as feed material.

Additional steps for methods 10, 20 may be taken to increase plant growth and to further stimulate the production of ethanol. For instance, in order to increase ethanol formation and to prevent stagnation of the water, and eventual killing of the aquatic plants, a water agitation system may be incorporated to encourage the movement of water around and through the aquatic plants. This prevents the build up of ethanol and other plant waste materials adjacent to the plant and brings nutrients to the plant. It has been further found that agitation of the water promotes the suspension of water additives such as yeast. The agitation may include any form of wave movement through the plants or a sustained flow of water through the plants. Such a water movement system may be fluidly coupled to a circulation loop which removes the ethanol from the water after the water it is piped or otherwise directed from the cell and before the water is returned to the cell. While the water is outside the cell in such a system, nutrients, antibiotics, $O_2$, $CO_2$, yeast or any other required or desired additives may be added to the water. Additionally, a circulation loop may be used to also remove the $O_2$ from the water to create the anoxic condition.

The cell may be covered with one or more sealing barriers to prevent the unwanted introduction of oxygen into the cell and to better thermally control the cell. The sealing barrier would seal the cell to prevent fluid communication between the cell and the adjacent atmosphere. This will inhibit oxygen from entering the cell and will encourage the anaerobic process. The sealing barrier may be a translucent barrier to encourage the capturing of radiant heat from a light source which is either naturally and/or artificially used to provide light to the aquatic plants. The sealing barrier may or may not also constitute a light blocking barrier which is positioned on the cell to prevent light from entering the cell during the anaerobic process. The sealing and light blocking barriers may be made of conventional materials. However, it should be understood that a dwelling, tank or other structure constructed around the cell may also define sealing and light block barriers should they be used in such a capacity. It has been found that manipulating light and dark conditions can affect the manner in which the aquatic plants produce ethanol and sugars. For instance, some aquatic plants may be subjected to light for several continuous days defining a light phase followed by restriction to light for several continuous days defining a dark phase to better encourage the anaerobic, ethanol producing, process. One such plant, *Stuckenia pectinata*, has been shown to have a light phase for up to about 6 days after which its production of sugars levels off or reaches a predetermined optimal level. The term "day" is defined as 24 hours. This plant has a dark phase of between about 2 days and 30 days during which it may enter the anaerobic process and produce ethanol. Generally, the ratio of light phase to dark phase will be no more than 1:2 and as small as 1:10, with a more common ratio of between 1:2 and 1:7. It should be understood that during both of the first and second time frames, $CO_2$ may be added to the water to encourage both the formation of sugar and ethanol. It should also be understood that the term "light" which should be blocked only applies to those forms of radiation, or wavelengths of light, which act as a photosynthesis catalyst and is dependent upon the type of chemical receptors used by each plant. Finally, the ability to control the light and dark phases above and the ratios described herein are not applicable to all aquatic plants as certain plants may experience ethanol production after less than 4 hours of dark phase. For these types of aquatic plants, the ratio of light phase to dark phase may be greater than 2:1, though such aquatic plants may have different limitations with respect to ethanol production than experienced with plants such as *Stuckenia pectinata*.

It has also been found that by controlling the life cycles of the aquatic plants may be beneficial in lengthening the life spans of the aquatic plants. In particular, the life of some of the aquatic plants terminates after the flowering of those plants. This can be prevented by the cutting off of a top portion of the aquatic plants before they can flower. Such cutting will stop some of the aquatic plants from reaching the surface of the water and flowering.

While the methods 10, 20 are being practiced, bacterial blooms may occur which can be controlled by antibiotics, bi-sulfates, hops and other common practices. However, it has been discovered that that method 10 produces free carbohydrates, and in particular monosaccharides, which encourage bacterial growth within the cell. For this reason, it has been found to be beneficial to introduce ethanol producing yeasts into the cell for the purpose of decreasing the carbohydrate concentrations and inhibiting bacterial growth. A beneficial outcome of the addition of yeast is an increase in ethanol output. As with the anaerobic process, the general equation for this process is $C_6H_{12}O_6 \rightarrow 2CO_2 + 2C_2H_5OH$ and is well known in the arts. The yeast may require replacement, particularly after the anoxic condition has been established and maintained for more than about three days, though this is dependent upon the strain of yeast being used.

FIG. 2 depicts one method 20 particularly well suited for use in a single cell, though it should be understood that this method may also be used with multiple cells. This method 20 also utilizes all concepts discussed above and generally includes the placement of the aquatic plants in a cell. The cell itself may be sunken into the ground surface or in a dwelling foundation, a partially sunken tank structure or a fully above ground tank structure. The cell may have any particular shape, though a circular or loop type cell may be beneficial for encouraging the movement of water within the cell. The water may be moved in a conventional manner though one utilizing a gravity lift system may prove to be beneficial due to its lower power requirements.

The water is either oxygenated or allowed to remain oxygenated as light enters the cell during the light phase. Generally, the light phase is continued for between ½ day and 10 days to allow the aquatic plants to form sugars, though this time frame may be adjusted for plant specific requirements. The sealing barrier may be used at this time to conserve heat should such be necessary to obtain an optimal temperature for the particular aquatic plant or plants being used. After the termination of the light phase, the light blocking barrier is then placed over the cell to begin the dark phase and the water is made anoxic to encourage the anaerobic process.

During the above light and dark phases, the water may be pulled out from and reintroduced into the cell through a closed loop system which may include an access point to the water to allow all additives discussed above to be supplied to the water without over exposing the water to the atmosphere. The closed loop system may further include an ethanol removal assembly such as, but limited to, conventional air strippers. This will allow the ethanol to be removed continuously while leaving the light blocking barrier and sealing barrier in place.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A method of recovering ethanol from an aquatic plant, said method comprising the steps of:
    placing at least one aquatic plant selected from the family Potamogetonaceae in a container containing water;
    creating or allowing an oxygenated condition within said water to initiate or maintain aerobic plant metabolism to produce and store carbohydrates during said oxygenated condition;
    creating and maintaining an anoxic condition within said water by removing oxygen from the water to initiate and maintain anaerobic plant metabolism, said at least one aquatic plant releasing ethanol into the water during said anoxic condition;
    repeating the steps of creating anoxic and oxygenated conditions one or more times to repeatedly release ethanol into the water, and
    recovering ethanol from the water.

2. The method according to claim 1, further including the step covering said container with a light blocking cover to inhibit light from entering said container during said anoxic condition.

3. The method according to claim 2, wherein the step of covering said container with said light blocking cover defines a dark phase, said light blocking cover being removed during said oxygenated condition to define a light phase to expose said container to light.

4. The method according to claim 1, further including the step of adding yeast to said container.

5. The method according to claim 1, further including the step of introducing catalysts to increase anaerobic metabolism.

6. The method of claim 1, wherein the step of placing at least one aquatic plant in a container includes said at least one aquatic plant being the *Potamogeton pectinatus*.

7. The method of claim 1, wherein the container is covered with a sealing barrier to prevent oxygen from entering said container.

8. The method of claim 1, wherein the container is covered with a light cover to inhibit photosynthesis inducing light from entering said container.

9. A method of recovering ethanol from an aquatic plant, said method comprising the steps of:
    placing at least one aquatic plant in a container containing water, the at least one aquatic plant being a submersed aquatic herb;
    initiating and maintaining a light phase in the container by exposing the at least one aquatic plant to light that induces photosynthesis
    to initiate or maintain an aerobic plant metabolism to produce and store carbohydrates during said light phase;
    initiating and maintaining a dark phase in the containing by covering the container with a light blocking cover to inhibit light from entering the container;
    removing oxygen from the water during the dark phase to initiate anaerobic plant metabolism, said aquatic plant releasing ethanol into the water during said dark phase;
    repeating the steps of initiating and maintaining the light and dark phases one or more times to repeatedly release ethanol into the water; and
    recovering ethanol from the water.

10. The method according to claim 9, wherein said anaerobic plant metabolism is initiated or promoted during the dark phase by adding yeast to said container.

11. The method according to claim 9, further including the step of introducing catalysts to increase anaerobic plant metabolism during the dark phase.

12. The method of claim 9, wherein the step of placing at least one aquatic plant in a container includes said at least one aquatic plant being *Potamogeton pectinatus*.

13. The method according to claim 9, wherein the container is covered with a sealing barrier to prevent oxygen from entering said water.

14. The method of claim 9, wherein said dark phase is maintained for at least 2 days and said light phase has a duration being less than a 1:2 ratio with respect to said dark phase.

15. A method of recovering ethanol from an aquatic plant, said method comprising the steps of:
    placing at least one aquatic plant in a container containing water, the at least one aquatic plant being a submersed aquatic herb;
    creating and maintaining an anoxic condition within said water to initiate and maintain anaerobic plant metabolism while inhibiting aerobic plant metabolism therein to produce ethanol, said at least one aquatic plant releasing ethanol into the water during said anoxic condition;
    creating and maintaining an oxygenated condition within said water to initiate and maintain aerobic plant metabolism while inhibiting anaerobic plant metabolism therein to produce and store carbohydrates during said oxygenated condition;
    repeating the steps of creating anoxic and oxygenated conditions one or more times to repeatedly release ethanol into the water, and
    recovering ethanol from said water.

16. The method of claim 15, wherein said at least one aquatic plant comprises the *Potamogeton pectinatus*.

17. The method according to claim 15, wherein the at least one aquatic plant is selected from the group of plant families consisting of Aponogetonaceae, Potamogetonaceae, Cymodoceaceae, Hydrocharitaceae, Ruppiaceae, Posidoniaceae, Haloragaceae, Ceratophyllaceae and Zosteraceae.

18. A method of recovering ethanol from an aquatic plant, said method comprising the steps of:
    placing at least one aquatic plant in a container containing water, the at least one aquatic plant being a submersed aquatic herb;
    creating or allowing an oxygenated condition within said water to initiate or maintain aerobic plant metabolism to produce and store carbohydrates during said oxygenated condition;
    creating and maintaining an anoxic condition within said water by removing oxygen from the water to initiate and maintain anaerobic plant metabolism, said at least one aquatic plant releasing ethanol into the water during said anoxic condition;
    repeating the steps of creating anoxic and oxygenated conditions one or more times to repeatedly release ethanol into the water, and
    recovering ethanol from the water.

19. The method according to claim 18, further including the step covering said container with a light blocking cover to inhibit light from entering said container during said anoxic condition.

20. The method according to claim 19, wherein the step of covering said container with said light blocking cover defines a dark phase, said light blocking cover being removed during said oxygenated condition to define a light.

21. The method according to claim 18, further including the step of adding yeast to said container.

22. The method according to claim 18, further including the step of introducing catalysts to increase anaerobic metabolism.

23. The method of claim 18, wherein said at least one aquatic plant comprises the *Potamogeton pectinatus*.

24. The method according to claim 18, wherein the at least one aquatic plant is selected from the group of plant families consisting of Aponogetonaceae, Potamogetonaceae, Cymodoceaceae, Hydrocharitaceae, Ruppiaceae, Posidoniaceae, Haloragaceae, Ceratophyllaceae and Zosteraceae.

* * * * *